US005104493A

United States Patent [19]
Chong

[11] Patent Number: 5,104,493
[45] Date of Patent: Apr. 14, 1992

[54] TERTIARY BUTYL HYDROPEROXIDE CONCENTRATION

[75] Inventor: Victor M. Chong, Media, Pa.

[73] Assignee: Arco Chemical Technology, L.P., Wilmington, Del.

[21] Appl. No.: 645,434

[22] Filed: Jan. 24, 1991

[51] Int. Cl.$^5$ .................. B01D 3/10; C07C 29/80; C07C 409/04
[52] U.S. Cl. ............................ 203/91; 203/6; 568/571; 568/576; 568/913
[58] Field of Search ............... 203/6, 91; 568/576, 568/571, 913

[56] References Cited

U.S. PATENT DOCUMENTS

| | | | |
|---|---|---|---|
| 2,383,919 | 8/1945 | Rust | 568/576 |
| 2,845,461 | 7/1958 | Winkler et al. | |
| 3,427,229 | 2/1969 | Herzog | 203/63 |
| 3,445,523 | 5/1969 | Rosenthal et al. | |
| 3,449,217 | 6/1969 | Harvey | 203/6 |
| 3,478,108 | 11/1969 | Grane | |
| 3,519,690 | 7/1970 | Joris | 568/576 |
| 3,864,216 | 2/1975 | Worrell et al. | 203/50 |
| 4,036,905 | 7/1977 | Kornfeld | |
| 4,128,587 | 12/1978 | Jubin | 568/571 |
| 4,257,852 | 3/1981 | Worrell | 203/71 |
| 4,317,801 | 3/1982 | Taylor et al. | 423/54 |
| 4,381,222 | 4/1983 | Brossmann et al. | 568/576 |
| 4,408,081 | 10/1983 | Foster | 568/571 |
| 4,584,413 | 4/1986 | Thornton | 568/576 |
| 4,900,850 | 2/1990 | Sanderson et al. | 549/529 |
| 4,910,349 | 3/1990 | Sanderson et al. | 568/909.8 |
| 4,912,266 | 3/1990 | Sanderson et al. | 568/909.8 |
| 4,912,267 | 3/1990 | Sanderson et al. | 568/909.8 |
| 4,922,033 | 5/1990 | Sanderson et al. | 568/909.8 |
| 4,922,034 | 5/1990 | Sanderson et al. | 568/909.8 |
| 4,922,035 | 5/1990 | Sanderson et al. | 568/909.8 |
| 4,922,036 | 5/1990 | Sanderson et al. | 568/909.8 |
| 4,992,566 | 2/1991 | Marquis et al. | 549/529 |
| 4,992,602 | 2/1991 | Sanderson et al. | 568/909.8 |

OTHER PUBLICATIONS

Winkler et al., *Liquid Phase Oxidation of Isobutane;* Industrial and Engineering Chemistry, vol. 53, pp. 655–658 (1961).

*Primary Examiner*—Wilbur Bascomb, Jr.
*Attorney, Agent, or Firm*—William C. Long

[57] ABSTRACT

The invention relates to a process for concentrating TBHP while avoiding flammability and explosion hazards by distilling a mixture of TBHP and TBA under reduced pressure of up to 300 mm Hg and separating a liquid TBHP concentrate containing at least 65 wt. % TBHP.

4 Claims, No Drawings

TERTIARY BUTYL HYDROPEROXIDE CONCENTRATION

BACKGROUND OF THE INVENTION

1. Field of the Invention

The present invention relates to the production of solutions of tertiary butyl hydroperoxide (TBHP) in tertiary butyl alcohol (TBA) which are highly concentrated in TBHP, i.e. 65 wt.% or higher.

2. Description of Prior Art

Methods are known for the production of TBHP by the molecular oxygen oxidation of isobutane at elevated temperature and pressure. In this regard, attention is drawn to U.S. Pat. No. 2,845,461 of Winkler, et al., to U.S. Pat. No. 3,478,108 of Grane and to U.S. Pat. No. 4,408,081 of Foster, et al.

In general, as a result of the molecular oxygen oxidation of isobutane as described in literature such as above-cited, there is formed a reaction mixture comprised of unreacted isobutane, TBHP and TBA which is also formed during the oxidation reaction and/or used as a stabilizing additive. U.S. Pat. No.4,128,587 shows the addition of TBA to the isobutane feed to such an oxidation zone. Isobutane, which has a normal boiling point much lower than that of either TBHP or TBA, can be readily separated from the oxidation mixture. However, the separation of TBHP and TBA is much more difficult and hazardous.

In many instances, the relative amounts of TBHP and TBA which are produced result in oxidation product mixtures comprised of 55% by weight or less of TBHP based on the total of TBHP plus TBA after removal of unreacted isobutane. In certain applications it is advantageous to employ solutions of TBHP in TBA which are more highly concentrated in TBHP, especially solutions which comprise 65 wt.% or more TBHP based on the total of TBHP plus TBA. However, normal distillation procedures are hazardous since at higher liquid concentrations of TBHP, distillate vapor tends to involve explosive concentrations of TBHP.

U.S. Pat. No.3,427,229 of Herzog shows use of a fluxing agent to prevent accumulation of TBHP in the vapors removed from an epoxidation reactor. It is indicated that hydroperoxide decomposition may present safety problems; see column 2, lines 1–4.

Harvey U.S. Pat. No.3,449,217 teaches the recovery of TBHP from isobutane oxidation mixtures by a procedure involving neutralization, dilution with water, and distillation at reduced pressure with a water/TBHP azeotrope recovered overhead, condensed and phase separated.

Worrell, et al. U.S. Pat. No.3,864,216 describes purifying TBHP from isobutane oxidation mixtures by neutralization, water addition and atmospheric pressure distillation with the use of a diluent gas.

Worrell U.S. Pat. No.4,257,852 shows distillation of aqueous TBHP streams in an apparatus having flame arresting packing.

For certain applications, it would be useful to distill an isobutane oxidate reaction mixture comprised of TBHP and TBA without the addition of materials such as water in order to produce a mixture of TBHP and TBA comprised of 65 wt.% TBHP or more while avoiding flammability and explosion hazards during the distillation.

BRIEF DESCRIPTION OF THE INVENTION

In accordance with the present invention, mixtures of TBHP and TBA such as are produced by the oxidation of isobutane are concentrated in TBHP to 65 wt.% TBHP and higher by distillation of the TBHP and TBA mixtures at reduced pressures of 300 mm Hg and lower, and especially at reduced pressures of 200 mm Hg and lower. It has been found that the relative volatility of TBHP is reduced somewhat in relation to that of TBA at low pressures and that, thus, for a given concentration of TBHP in the liquid phase the corresponding concentration of TBHP in the vapor phase is lower at the lower pressures. In addition, at the lower pressures, the flammable limit concentration of TBHP in the vapor phase is substantially increased. Finally, at the low distillation pressures, lower distillation temperatures are employed at which substantially lower TBHP decomposition rates are achieved.

DETAILED DESCRIPTION

In the process of the invention, a mixture comprised of TBHP and TBA, such as that resulting from isobutane oxidation after separation of unreacted isobutane, is vacuum distilled at an overhead pressure of not more than 300 mm Hg, preferably not more than 200 mm Hg, and most preferably not more than 100 mm Hg. Throughout the entirety of the distillation zone, explosive vapor compositions are avoided—i.e., the weight percent of TBHP in the vapor is maintained at a level which is below the flammable limit. In addition, low temperatures are maintained throughout the entire distillation zone, thus reducing TBHP decomposition and the yield loss and hazards associated with such decomposition.

It has been determined that higher concentrations of TBHP in TBHP/TBA mixtures can be tolerated in the vapor phase at low pressures without generating a flammable vapor. For example, whereas at atmospheric pressure for TBHP/TBA mixtures the flammable limit for TBHP in the vapor is about 38.5 wt.% which corresponds to 63 wt.% TBHP in the liquid phase. By contrast, at 100 mm Hg pressure, the flammable limit in the vapor for TBHP is 44 wt.% which corresponds to 71 wt. % TBHP in the liquid phase.

An additional advantage of the invention is that at the low distillation temperatures which accompany the low distillation pressures, there is less TBHP decomposition and thus safer and more efficient operation. The decomposition of TBHP in TBA/TBHP mixtures generates a significant quantity of free oxygen which lowers the flammable TBHP vapor composition and increases the possibility of explosion.

The TBHP/TBA mixtures which are concentrated in accordance with the present invention are most conveniently prepared by the oxidation of isobutane in accordance with conventional procedures such as described in U.S. Pat. No. 2,845,461. Oxidate mixtures from such reaction are generally first debutanized, i.e. the unreacted isobutane is stripped from the mixture leaving an oxidation product mixture mainly comprised of TBHP and TBA and also containing small amounts of organic by-products such as acetone, formic acid and the like. Generally speaking, the TBHP comprises about 30 to 55 wt.% of such mixtures. In many instances, it is desirable to concentrate the mixture in TBHP in order to provide a TBHP solution which has improved utility while avoiding TBHP decomposition and explosion hazards.

In accordance with the present invention, the mixture of TBHP and TBA containing less than 65 wt.% TBHP and usually 30 to 55 wt.% TBHP can be conveniently and safely concentrated to 65 wt.% or above TBHP in TBA by subjecting the mixture to a vacuum distillation. Conventional distillation apparatus can be employed. It is essential that the overhead distillation pressure be maintained at 300 mm Hg or lower, preferably 200 mm Hg or lower, in order to avoid the formation of hazardous and flammable vapor compositions during the distillation. The liquid bottoms temperatures employed during distillation are in the range of 70° to 80° C.; preferably the distillation bottoms temperature which is the highest temperature in the distillation is maintained no greater than 75° C. Where product concentrations of TBHP in excess of 70 wt.% are desired, it is essential that the vacuum distillation overhead pressure be maintained no greater than 100 mm Hg.

Through practice of the invention, solutions of TBHP in TBA can conveniently and safely be concentrated with respect to the TBHP to concentrations of 65 wt.% and even significantly higher.

In order to more clearly illustrate the invention, the following example is provided.

EXAMPLE

An isobutane oxidation reaction mixture after debutanizing and comprising 45 wt.% TBHP, 55 wt.% TBA and other impurities, is preheated to 62oC and continuously fed to a vacuum distillation column which has 9 theoretical distillation stages. The bottoms temperature is maintained at 71° C., heat being provided to the column by means of a conventional reboiler.

The overhead pressure is maintained at 100 mm Hg, overhead temperature at 39° C. and 31%C by weight of the feed is continuously removed as an overhead distillate product. The composition of the overhead stream is 1.1 wt.% TBHP and 98.9% TBA and other impurities.

A bottoms stream in amount of 69% by weight of the feed is removed from the distillation column continuously, and this stream has a composition of 65 wt.% TBHP, 35 wt.% TBA and other impurities. This bottoms stream is suitable for many applications where TBHP is employed. Most notably, this stream finds utility in the epoxidation of olefins such as propylene by known procedures to produce propylene oxide and co-product TBA.

By way of contrast, where comparable distillations are carried out at higher distillation pressures, TBHP cannot be concentrated to 65 wt.% or above without the formation of flammable TBHP mixtures unless alternate means such as the introduction of diluents and the like are employed. Such means provide an added expense and inconvenience and possibly involve the introduction of materials which are undesirable in the subsequent use of the concentrated TBHP mixtures.

I claim:

1. In a process for the production of a product stream consisting essentially of tertiary butyl hydroperoxide and tertiary butyl alcohol and containing 65 wt.% or more tertiary butyl hydroperoxide from a dubutanized isobutane oxidate mixture consisting essentially of tertiary butyl alcohol and up to 60 wt.% tertiary butyl hydroperoxide, the improvement which comprises distilling said debutanized oxidate mixture in a fractional distillation zone at a pressure of 300 mmHg or less to form vapor enriched in tertiary butyl alcohol and liquid enriched in tertiary butyl hydroperoxide, maintaining the concentration of the tertiary butyl hydroperoxide in the vapor in the distillation zone below the flammable limit concentration of said tertiary butyl hydroperoxide in the vapor mixture, separating an overhead vapor fraction enriched in tertiary butyl alcohol and consisting essentially of tertiary butyl alcohol and tertiary butyl hydroperoxide, and separating a liquid fraction consisting essentially of tertiary butyl alcohol and tertiary butyl hydroperoxide and containing 65 wt.% tertiary butyl hydroperoxide or higher.

2. The process of claim 1 wherein said pressure is 200 mm Hg or less.

3. The process of claim 1 wherein said pressure is 100 mm Hg or less.

4. The process of claim 1 wherein temperatures in the distillation zone do not exceed 80° C.

* * * * *

REEXAMINATION CERTIFICATE (2656th)

United States Patent [19]

Chong

[11] B1 5,104,493

[45] Certificate Issued Aug. 15, 1995

[54] TERTIARY BUTYL HYDROPEROXIDE CONCENTRATION

[75] Inventor: Victor M. Chong, Media, Pa.

[73] Assignee: Arco Chemical Technology, L.P., Wilmington, Del.

Reexamination Request:
No. 90/002,839, Sep. 18, 1992

Reexamination Certificate for:
Patent No.: 5,104,493
Issued: Apr. 14, 1992
Appl. No.: 645,434
Filed: Jan. 24, 1991

[51] Int. Cl.$^6$ .................. B01D 3/10; C07C 29/80; C07C 409/04

[52] U.S. Cl. ................................. 203/91; 203/6; 568/571; 568/576; 568/913

[56] References Cited

U.S. PATENT DOCUMENTS 4,992,566  2/1991  Marquis et al. ................. 549/529

FOREIGN PATENT DOCUMENTS 1232709  5/1971  United Kingdom .

*Primary Examiner*—Wilbur Bascomb, Jr.

[57] ABSTRACT

The invention relates to a process for concentrating TBHP while avoiding flammability and explosion hazards by distilling a mixture of TBHP and TBA under reduced pressure of up to 300 mm Hg and separating a liquid TBHP concentrate containing at least 65% wt. % TBHP.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 4 are determined to be patentable as amended.

Claims 2 and 3, dependent on an amended claim, are determined to be patentable.

1. In a process for the production of a product stream consisting essentially of tertiary butyl hydroperoxide and tertiary butyl alcohol and containing 65 wt. % or more tertiary butyl hydroperoxide from a [dubutanized] *debutanized* isobutane oxidate mixture consisting essentially of tertiary butyl alcohol and [up] *30 wt. % to* 60 wt. % tertiary butyl hydroperoxide, the improvement which comprises distilling said debutanized oxidate mixture in a fractional distillation zone *at a temperature which does not exceed 80° C. and* at a pressure of 300 mmHg or less to form vapor enriched in tertiary butyl alcohol and liquid enriched in tertiary butyl hydroperoxide, maintaining the concentration of the tertiary butyl hydroperoxide in the vapor in the distillation zone below the flammable limit concentration of said tertiary butyl hydroperoxide in the vapor mixture, separating an overhead vapor fraction enriched in tertiary butyl alcohol and consisting essentially of tertiary butyl alcohol and tertiary butyl hydroperoxide, and separating a liquid fraction consisting essentially of tertiary butyl alcohol and tertiary butyl hydroperoxide and containing 65 wt. % tertiary butyl hydroperoxide or higher.

4. The process of claim 1 wherein temperatures in the distillation zone do not exceed [80] *75°* C.

* * * * *